United States Patent [19]

Ikeda et al.

[11] Patent Number: 4,814,461

[45] Date of Patent: * Mar. 21, 1989

[54] PROCESS FOR PREPARING E-ISOMER OF A TRIAZOLYL STYRYL KETONE DERIVATIVE

[75] Inventors: Takaharu Ikeda, Toyonaka; Kazuhiro Tada, Kyoto, both of Japan

[73] Assignee: Sumitomo Chemical Company, Limited, Osaka, Japan

[*] Notice: The portion of the term of this patent subsequent to Mar. 21, 2006 has been disclaimed.

[21] Appl. No.: 7,655

[22] Filed: Jan. 28, 1987

[30] Foreign Application Priority Data

Jan. 31, 1986 [JP] Japan .................. 61-020697

[51] Int. Cl.$^4$ ........................... C07D 249/12
[52] U.S. Cl. ..................... 548/262; 568/310
[58] Field of Search ............... 548/262; 568/384, 310, 568/341

[56] References Cited

U.S. PATENT DOCUMENTS 4,018,718 4/1977 Ochsner et al. ............... 568/341

FOREIGN PATENT DOCUMENTS

| 57-102872 | 6/1982 | Japan | 548/262 |
| 58-140081 | 8/1983 | Japan | 548/262 |
| 58-140082 | 8/1983 | Japan | 548/262 |
| 58-146575 | 8/1983 | Japan | 548/262 |
| 58-174373 | 10/1983 | Japan | 548/262 |

OTHER PUBLICATIONS

Baranyai et al., "Determination of the Geometric, etc.", CA 95:169538d (1981).
Cobb et al., "Isomerization of Cis, Tranc, etc.", CA 87:200936t (1977).

*Primary Examiner*—Glennon H. Hollrah
*Assistant Examiner*—Patricia L. Morris
*Attorney, Agent, or Firm*—Birch, Stewart, Kolasch & Birch

[57] ABSTRACT

A novel process for preparing E-isomer of a triazolyl styryl ketone derivative of the formula (I):

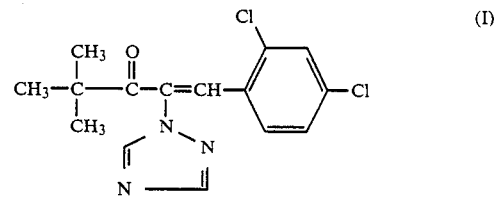

which includes treating Z-isomer of the derivative (which may contain E-isomer of the derivative) with sulfuric acid and an isomerization catalyst in an organic solvent, precipitating and separating the resulting sulfuric acid salt of E-isomer from the solution, and decomposing the resulting precipitate to obtain E-isomer of the derivative free from sulfuric acid. The E-isomer is useful for preparing E-isomer of triazolyl styryl carbinol of the formula (II):

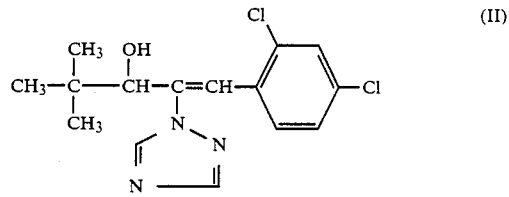

which is useful as an antimicrobial agent, a herbicide, a plant growth regulator, or the like.

13 Claims, No Drawings

PROCESS FOR PREPARING E-ISOMER OF A TRIAZOLYL STYRYL KETONE DERIVATIVE

The present invention relates to a novel process for preparing the E-isomer of 1-(2,4-dichlorophenyl)-2-(1,2,4-triazol-1-yl)-4,4-dimethyl-1-penten-3-one (hereinafter referred to as "triazolyl styryl ketone derivative") of the formula (I):

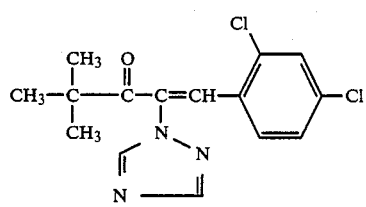

BACKGROUND OF THE INVENTION

It is known that the triazolyl styryl ketone derivative (I) itself is useful as an antimicrobial agent [cf. Japanese Patent First Publication (Kokai) No. 130661/1978], and that triazolyl styryl carbinol of the formula (II):

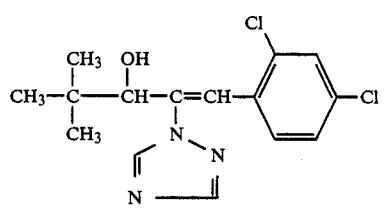

which is obtained by reduction of the above derivative (I), is more useful as an antimicrobial agent, a herbicide, a plant growth regulator, or the like. It is also known that the effect of E-isomer thereof is particularly superior to that of the Z-isomer [cf. Japanese Patent First Publication (Kokai) No. 41875/1979, 124771/1980 and 25105/1981].

Accordingly, it is desired to provide a process for efficiently preparing the E-isomer of the triazolyl styryl ketone dirivative of the above formula (I) which is a starting material for preparing the E-isomer of the above compound of the formula (II) (hereinafter E-isomer, Z-isomer and a mixture of E-isomer and Z-isomer of the triazolyl styryl ketone derivative (I) are simply referred to as "E-isomer", "Z-isomer" and "E/Z-isomer", respectively, unless specified otherwise). As a process for satisfying such a requirement, for example, the following processes are proposed:

(1) A process of isomerizing Z-isomer or E/Z-isomer into E-isomer with light [cf. Japanese Patent First Publication (Kokai) No. 147265/1980].

(2) A process of isomerizing Z-isomer or E/Z-isomer with a compound such as an aromatic mercaptan [cf. Japanese Patent First Publication (Kokai) No. 147265/1980].

(3) A process of separating E/Z-isomer with chromatography [cf. Japanese Patent First Publication (Kokai) No. 147265/1980].

(4) A process of separating E-isomer from E/Z-isomer, which comprises treating E/Z-isomoer with sulfuric acid, precipitating and separating the sulfuric acid salt of E-isomer, and decomposing the salt to obtain E-isomer [cf. Japanese Patent First Publication (Kokai) No. 140081/1983].

However, these processes have problems such as, for example, the necessity of a special reaction apparatus or the necessity of an additional treatment for separating E- and Z-isomers from the reaction products because of an insufficient isomerization rate. Moreover, in the case of the process for merely separating E-isomer from E/Z-isomer such as the process (4), the yield of E-isomer is dependent on the E-isomer content contained in the starting E/Z-isomer and the treatment of the residual Z-isomer is also necessary.

BRIEF DESCRIPTION OF THE INVENTION

In view of the above circumstances, the present inventors have extensively investigated as to a process which is free from the above problems and can provide easily and effectively the desired E-isomer from Z-isomer or E/Z-isomer on an industrial scale and in a good yield, and have found a process which can perform simultaneously the isomerization of Z-isomer or E/Z-isomer and the separation of E-isomer and can satisfy the above-mentioned requirements.

Thus, the object of the present invention is to provide a novel process for preparing E-isomer of the triazolyl styryl ketone derivative of the above formula (I), which comprises treating Z-isomer of the derivative which may contain E-isomer with sulfuric acid and an isomerization catalyst in an organic solvent, precipitating and separating the resulting sufuric acid salt of E-isomer from the solution, and decomposing the precipitate to obtain E-isomer of the derivative free from the sulfuric acid.

DETAILED DESCRIPTION OF THE INVENTION

The starting material used in the present invention may be either Z-isomer or E/Z-isomer, i.e. a mixture of E-isomer and Z-isomer wherein the E-isomer content is not limited.

The sulfuric acid used in the present invention is a sulfuric acid having a high concentration of not lower than 40% by weight, preferably not lower than 50% by weight, more preferrably not lower than 90% by weight. The sulfuric acid is usually used in an amount of 0.5 to 3 moles, preferably 0.8 to 1.2 moles, per 1 mole of the starting Z-isomer or E/Z-isomer.

The isomerization catalyst used in the present invention is not limited and may be any isomerization catalyst which has an ability to isomerize Z-isomer into E-isomer in the presence of sulfuric acid. The preferable isomerization catalyst is compound which can release a halonium ion, and includes, for example, halogens (e.g. chlorine, bromine, iodine, etc.), halohalides, (e.g. iodine monobromide, etc.), halocyanides (e.g. cyanogen bromide, etc.), N-halocarboxylic amides or N-halodicarboxylic imides (e.g. N-bromosuccinimide, N-bromoacetamide, N-bromocaprolactam, N-bromophthalimide, etc.), hypohalogenous acids (e.g. trifluoroacetyl hypobromite, etc.), complexes of a halogen with an organic compound (e.g. triphenylphosphine dibromide, etc.), and the like. In the above halogen ion-releasing compound, the particularly preferable one is bromine ion-releasing compound. The isomerization catalyst is usually used in an amount of 0.0001 to 1.0 mole, preferably 0.001 to 0.1 mole, per 1 mole of the starting Z-isomer or Z-isomer contained in E/Z-isomer.

The solvent used in the present invention is not limited and includes, preferably, aprotic organic solvents, for example, aromatic hydrocarbons (e.g. benzene, xylene, toluene, etc.), halogenated hydrocarbons (e.g. dichloromethane, chloroform, carbon tetrachloride, dichloroethane, trichlene, perchlene, monochlorobenzene, dichlorobenzene, etc.), esters (e.g. ethyl acetate, ethyl formate, etc.), ethers (e.g. diethyl ether, tetrahydrofuran, etc.), aliphatic or alicyclic hydrocarbons (e.g. hexane, heptane, octane, petroleum ether, cyclohexane, etc.), and a mixture thereof. Although the amount of the solvent varies largely depending on, for example, the kind of the solvent, the kind of the isomerization catalyst, and the like, it is usually used in an amount of 0.5 to 20-fold by weight of the starting Z-isomer or E/Z-isomer.

The reaction is usually carried out at a temperature of from 0° to 200° C., preferably from 30° to 150° C., for 0.5 to 48 hours.

The isomerization of Z-isomer into E-isomer proceeds by treating Z-isomer or E/Z-isomer with sulfuric acid and an isomerization catalyst, by which a sulfuric acid salt of E-isomer is produced. After the reaction, the reaction mixture is cooled to precipitate the salt of E-isomer from the mixture. In general, the sulfuric acid salt of E-isomer precipitates spontaneously, as a crystal, from the reaction mixture with the progress of the reaction, while a seed crystal may be used to ensure the precipitation of the salt.

The separation of the precipitated sulfuric acid salt of E-isomer from the reaction mixture is carried out by a conventional method such as filtration, centrifugation, decantation, or the like.

The recovery of E-isomer from the sulfuric acid salt of E-isomer is carried out by salt-decomposition or neutralization of the resulting sulfuric acid salt. For example, the sulfuric acid salt of E-isomer can be decomposed by mixing the salt with an excess of water and a solvent which is immiscible with water and can dissolve E-isomer (e.g. toluene, monochlorobenzene, etc.), to obtain a high purity of E-isomer from the organic layer. The decomposition of the sulfuric acid salt of E-isomer may also be carried out by using a protic solvent except water (e.g. methanol, acetic acid, etc.). Alternatively, E-isomer can be obtained by neutralizing the salt thereof with an aqueous solution of a base such as sodium hydroxide, sodium bicarbonate, sodium carbonate, or the like.

According to the present invention, Z-isomer can easily be isomerized into E-isomer in a good yield on an industrial scale, without using a special apparatus. Moreover, a high purity of E-isomer which is substantially free of any by-product can be obtained.

The present invention is illustrated by the following Examples, but should not be construed to be limited thereto. In the Examples, "%" and "ratio" mean "% by weight" and "ratio by weight", respectively, unless specified otherwise.

Example 1

Z-isomer of 1-(2,4-dichlorophenyl)-2-(1,2,4-triazol-1-yl)-4,4-dimethyl-1-penten-3-one (5.00 g; purity of Z-isomer: 100.0%) was dissolved in o-dichlorobenzene (20 g), and thereto were added dropwise conc. sulfuric acid (1.50 g; sulfuric acid content: 97%) and then bromine (0.0750 g) at 20° C. After reacting the mixture at a temperature of from 90° C. to 100° C. for 3 hours, the mixture was cooled to 20° C., and the resulting crystals were separated by filtration. The crystals were washed twice with chloroform (20 g) to give sulfuric acid salt of E-isomer (6.21 g). To the crystals (1.00 g) were added 10% aqueous sodium bicarbonate (4 g), chloroform (30 g) and water (20 g). After stirring the mixture at room temperature till the crystals disappeared, the aqueous layer was removed from the mixture, and the chloroform layer was washed twice with water and then concentrated to obtain E-isomer of 1-(2,4-dichlorophenyl)-2-(1,2,4-triazol-1-yl)-4,4-dimethyl-1-penten-3-one. The yield of E-isomer to the starting Z-isomer was 93.3%, and the ratio of E-isomer to Z-isomer (hereinafter referred to as "E/Z ratio", unless specified otherwise) was 100/0.

Examples 2 to 4

Using the same amount of Z-isomer as used in Example 1, Example 1 was repeated to obtain E-isomer, except that a kind of solvent and an amount thereof, a kind of isomerization catalyst and an amount thereof, a reaction temperature and a reaction time as shown in Table 1 were employed. The results are shown in Table 1.

TABLE 1

| | Solvent | | Isomerization catalyst | | Reaction temperature (°C.) | Reaction time (hrs) | Yield of E-isomer (%) | E/Z ratio (by weight) |
|---|---|---|---|---|---|---|---|---|
| | Kind | Amount (g) | Kind | Amount (g) | | | | |
| Ex. 2 | Monochlorobenzene | 20 | Bromine | 0.075 | 90–100 | 4.5 | 92.6 | 100/0 |
| Ex. 3 | o-Dichlorobenzene | 10 | N—Bromosuccinimide | 0.25 | " | 3.5 | 84.8 | " |
| Ex. 4 | o-Dichlorobenzene | 20 | Iodine | 0.5 | 120 | 24 | 50.7 | " |

Example 5

A crude mixture f E-isomer and Z-isomer of 1-(2,4-dichlorophenyl)-2-(1,2,4-triazol-1-yl)-4,4-dimethyl-1-penten-3-one (18.5 g; E/Z ratio: 40.6/59.4; purity of E/Z-isomer mixture: 90.1%) was dissolved in monochlorobenzene (51.5 g), and thereto were added dropwise n-heptane (10 g) and conc. sulfuric acid (5.59 g; sulfuric acid content: 97%). Then, bromine (0.273 g) was added to the mixture, and the mixture was allowed to react at a temperature of from 100° to 110° C. for 3 hours. After the reaction, the mixture was cooled to 20° C., and the resulting crystals were separated by filtration. The crystals were washed twice with chloroform (40 g) to give sulfuric acid salt of E-isomer (22.0 g). To the crystals (15.0 g) were then added 10% aqueous sodium bicarbonate (150 g) and chloroform (150 g), and the mixture was stirred at room temperature until the crystals disappeared. The aqueous layer was then removed from the mixture, and the chloroform layer was washed twice with water and concentrated to obtain E-isomer of 1-(2,4-dichlorophenyl)-2-(1,2,4-triazol-1- yl)-4,4-dimethyl-1-penten-3-one. The yield of E-isomer to the net E-isomer/Z-isomer mixture contained in the starting crude mixture was 86.4%, and the E/Z ratio was 99.0/1.0.

Example 6

A crude E-isomer/Z-isomer mixture of 1-(2,4-dichlorophenyl)-2-(1,2,4-triazol-1-yl)-4,4-dimethyl-1-penten-3-one (30.0 g; E/Z ratio: 40.0/59.1; purity of E/Z-isomer mixture: 87.9%) was dissolved in monochlorobenzene (80.0 g), and thereto was added dropwise conc. sulfuric acid (10.1 g; sulfuric acid content: 98.5%). To the mixture was then added bromine (0.44 g), and the mixture was allowed to react at 85° C. for 6 hours. After the reaction, the mixture was slowly cooled to 20° C., and the resulting crystals were separated by filtration. The crystals were washed twice with monochlorobenzene (40 g) to give sulfuric acid salt of E-isomer (39.5 g). To the crystals (39.5 g) were then added water (150 g) and monochlorobenzene (150 g), and the mixture was stirred at 50° C. until the crystals disappeared. The aqueous layer was then removed from the mixture, and the monochlorobenzene layer was washed with water and concentrated to obtain E-isomer of 1-(2,4-dichlorophenyl)-2-(1,2,4-triazol-1-yl)-4,4-dimethyl-1-penten-3-one. The yield of E-isomer to the net E-isomer/Z-isomer mixture contained in the starting crude mixture was 96.4%, and the E/Z ratio was 99.0/1.0.

What is claimed is:

1. A process for preparing the E-isomer of triazolyl styryl ketone derivative of the formula (I):

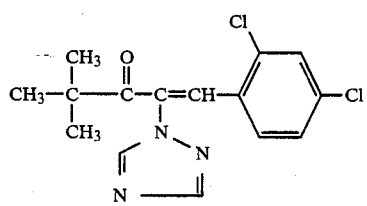

which comprises
treating the Z-isomer of said derivative which may contain E-isomer of said derivative with sulfuric acid and an isomerization catalyst, which catalyst is capable of releasing a halonium ion, in an organic solvent,
precipitating and separating the resulting sulfuric acid salt of the E-isomer from the solution, and
decomposing the resulting precipitate to obtain the E-isomer of said derivative free from sulfuric acid.

2. The process according to claim 1, wherein the halonium ion is bromonium ion.

3. The process according to claim 1, wherein the isomerization catalyst is a member selected from the group consisting of a halogen, iodine monobromide, a cyanogen halide, N-bromosuccinimide, N-bromoacetamide, N-bromocaprolactam, N-bromophthalimide, trifluoroacetyl hypobromite, and triphenylphosphine dibromide.

4. The process according to claim 3, wherein the halogen is bromine.

5. The process according to claim 1, wherein the isomerization catalyst is used in an amount of 0.0001 to 1.0 mole per 1 mole of the starting Z-isomer or Z-isomer contained in E/Z-isomer.

6. The process according to claim 1, wherein the sulfuric acid is a sulfuric acid having a concentration of not lower than 40% by weight.

7. The process according to claim 1, wherein the sulfuric acid is used in an amount of 0.5 to 3 moles per 1 mole of the starting Z-isomer or E/Z-isomer.

8. The process according to claim 1, wherein the reaction is carried out at a temperature of from 30° C. to 150° C.

9. The process according to claim 1, wherein the precipitated and separated sulfuric acid salt of E-isomer is decomposed by mixing said salt with a mixture of water and a solvent which is immiscible with water and can dissolve E-isomer.

10. The process according to claim 9, wherein the sulfuric acid salt of E-isomer is neutralized and decomposed by further adding an alkali.

11. The process according to claim 1, wherein the solvent is a member selected from the group consisting of benzene, xylene, toluene, dichloromethane, chloroform, carbon tetrachloride, dichloroethane, trichlene, perchlene, monochlorobenzene, dichlorobenzene, ethyl acetate, ethyl formate, diethyl ether, tetrahydrofuran, hexane, heptane, octane, petroleum ether, and cyclohexane.

12. The process according to claim 1, wherein the solvent is used in an amount of 0.5 to 20-fold by weight of the starting Z-isomer or E/Z isomer.

13. The process according to claim 1, which is carried out for 0.5 to 48 hours.

* * * * *